United States Patent [19]

Suzuki et al.

[11] Patent Number: 5,032,170
[45] Date of Patent: Jul. 16, 1991

[54] PLANT GROWTH PROMOTION

[75] Inventors: Akinori Suzuki, Chiba; Be H. Suong, Urawa; Akinori Tanaka, Niigata; Masakazu Furushima, Nagareyama; Kazuko Tamano, Toyosaka; Yuko Ebe, Toyosaka; Noriko Tamano, Toyosaka; Akiko Tamano, Toyosaka, all of Japan

[73] Assignee: Mitsubishi Gas Chemical Company, Ltd., Tokyo, Japan

[21] Appl. No.: 610,441

[22] Filed: Nov. 5, 1990

Related U.S. Application Data

[63] Continuation of Ser. No. 870,394, Jun. 4, 1986, abandoned.

[30] Foreign Application Priority Data

Jun. 7, 1985 [JP] Japan .................................. 60-123812

[51] Int. Cl.$^5$ ..................... A01N 33/02; C07C 215/08
[52] U.S. Cl. ........................................ 71/121; 564/291
[58] Field of Search ........................... 71/121; 564/291

[56] References Cited

U.S. PATENT DOCUMENTS

| 3,542,538 | 11/1970 | Limburgerhof et al. | 71/121 |
| 4,309,205 | 1/1982 | Kessler | 71/121 X |
| 4,799,950 | 1/1989 | Suzuki et al. | 71/121 |
| 4,929,267 | 5/1990 | Suzuki et al. | 71/77 |

Primary Examiner—Glennon H. Hollrah
Assistant Examiner—S. Mark Clardy
Attorney, Agent, or Firm—Wenderoth, Lind & Ponack

[57] ABSTRACT

This invention relates to use of compounds of the formula

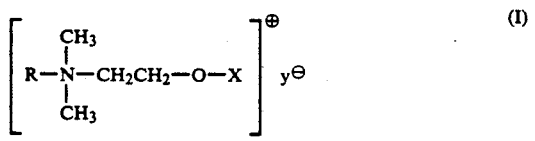

wherein R represents a $C_{2-5}$ alkyl, $C_{2-5}$ alkenyl or $C_{2-5}$ alkynyl group, and X represents a hydrogen atom, a $C_{2-8}$ alkylcarbonyl, carbamoyl, benzoyl, chloromethylcarbonyl or methoxycarbonyl group, or $-PO_3H_2$, and Y represents a chlorine or bromine atom in promoting the growth of plants.

9 Claims, No Drawings

PLANT GROWTH PROMOTION

This application is a continuation of now abandoned application Ser. No. 06/870,394 filed on June 4, 1986, now abandoned.

This invention relates to the promotion of plant growth, and more specifically, to a method of promoting the photosynthetic action and root-forming action of a plant and promoting its growth.

One method of increasing the ability of a plant to produce a substance is to increase its photosynthetic ability. Some attempts have been made to promote the photosynthesis of plants by selecting substrates or employing chemical means. For example, choline salts are known to have a plant growth promoting effect. U.S. Pat. No. 4,309,205 discloses a method of increasing the quantity and quality of flowers and fruits of a plant growing in soil which comprises applying to a mature plant during its reproductive stage a flower or fruit quantity and quality improving effective amount of at least one non-toxic salt of choline in an aqueous medium. U.S. Pat. No. 4,488,901 discloses a method of increasing the cold resistance of a plant, which comprises treating a cultivated plant before a temperature drop with an aqueous solution of at least one compound of the formula HO—CH$_2$—$_n$NH$_2$ wherein n is an integer of 2 to 5 or its N,N,N-trimethyl-quaternary ammonium salt thereof.

The present inventors have long worked in search of a substance capable of effectively promoting the photosynthetic and root-forming action of plants by chemical treatment, and have now found that a certain aminoethanol derivative has the ability to promote the photosynthetic and root-forming actions of plants significantly.

According to this invention, there is provided a method of promoting the growth of plants, which comprises applying an effective amount of at least one active compound selected from the group consisting of compounds of the formula

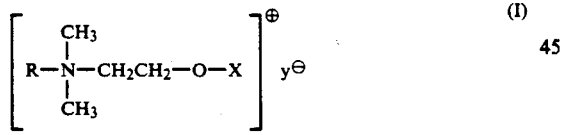

wherein R represents a C$_{2-5}$ alkyl, C$_{2-5}$ alkenyl or C$_{2-5}$ alkynyl group, and X represents a hydrogen atom, a C$_{2-8}$ alkylcarbonyl, carbamoyl, benzoyl, chloromethylcarbonyl or methoxycarbonyl group, or —PO$_3$H$_2$, and Y represents a chlorine or bromine atom to the stalks, leaves, roots or seeds of the plants.

In formula (I), the C$_{2-5}$ alkyl group represented by R may be linear or branched, and includes, for example, ethyl, n-propyl, iso-propyl, n-butyl, isobutyl, sec-butyl, tert-butyl, n-pentyl and tert-pentyl. The C$_{2-5}$ alkenyl may also be linear or branched, and includes, for example, vinyl, allyl, methallyl, 2-butenyl, 3-butenyl, and 2-(3-methyl)butenyl. Examples of the C$_{2-5}$ alkynyl group are ethynyl, 2-propynyl and butynyl.

The alkyl moiety of the C$_{2-8}$ alkylcarbonyl group represented by X may be linear or branched, and specific examples of the C$_{2-8}$ alkylcarbonyl group include acetyl, propionyl, n-butyryl, isobutyryl, n-valeryl, caproyl and capryloyl.

Alkyl groups having 2 to 4 carbon atoms and a methallyl group are preferred as R, and X is preferably a hydrogen atom or a C$_{2-4}$ alkylcarbonyl group.

The agriculturally acceptable salts of the compounds of formula (I) include, for example, hydrohalogenates such as hydrochlorides and hydrobromides, inorganic acid salts such as phosphates, nitrates, sulfates and carbonates, and organic acid salts such as acetates, citrates, lactates and L(+)-tartrates. Of these, the hydrochlorides and hydrobromides are preferred.

The compounds of formula (I) or its salt can be produced, for example, by (a) reacting an N,N-dimethylethanoline represented by the formula

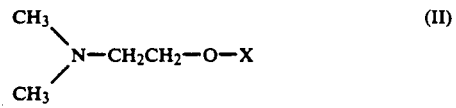

wherein X is as defined hereinabove, with a halide represented by the formula

wherein Hal represents a halogen atom, and R is as defined above, to obtain a compound represented by the following formula

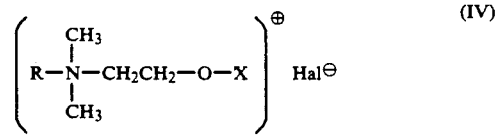

wherein R is as defined above, or (b) reacting a compound of formula (IV) in which X is a hydrogen atom with a C$_{2-8}$ alkylcarbonyl halide, C$_{2-8}$ alkanoic acid anhydride, carbamoyl halide, benzoyl halide, chloroacetyl halide or phosphoric acid to form a compound of formula (I) wherein X is as defined but other than a hydrogen atom.

Some embodiments of their production are shown below.

PRODUCTION EXAMPLE 1

A 100 ml eggplant-shaped flask was charged with 8.91 g of N,N-dimethylethanolamine, and 30 ml of diethyl ether was added. The mixture was stirred, and 11.45 g of allyl chloride was added. The mixture was stirred at room temperature for 2 days. The resulting white precipitate was collected by suction filtration, well washed with dimethyl ether, and dried in a desiccator under reduced pressure to give 9.01 g (yield 55%) of a compound of the following formula

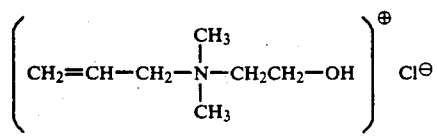

(compound No. 4 in Table 1 given hereinbelow).

PRODUCTION EXAMPLE 2

A 50 ml eggplant-shaped flask was charged with 4.46 g of N,N-dimethylethanolamine and 7.0 g of n-butyl bromide, and the mixture was stirred at room temperature for 15 hours, and then worked up as in Production Example 1 to give 10.46 g (yield 93%) of a compound of the following formula

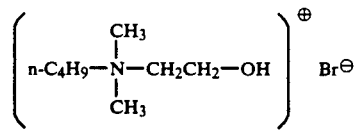

(compound No. 3 in Table 1 given hereinbelow).

PRODUCTION EXAMPLE 3

A 50 ml eggplant-shaped flask was charged with 4.24 g (20 mmoles) of a compound of the formula

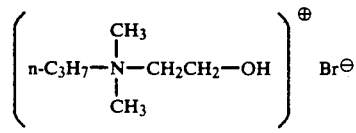

and 10.21 g (100 mmoles) of acetic anhydride, and they were reacted at 100° C. for 5 hours. After cooling, anhydrous ether was added to precipitate a compound (compound No. 15 in Table 1) of the formula

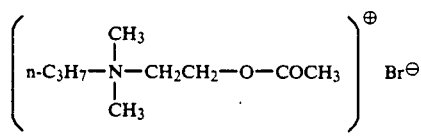

as crystal. The crystals were collected by suction filtration, dried, and dissolved in anhydrous ethanol. Anhydrous ether was added, and the crystals were recrystallized from anhydrous ether. Yield: 72.6%.

PRODUCTION EXAMPLE 4

3.07 g (20 mmoles) of a compound of the formula

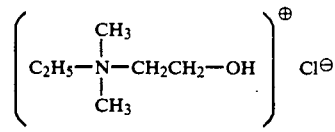

and 14.06 g (100 mmoles) of benzoyl chloride were reacted as in Production Example 3. Recrystallization gave a compound (compound No. 18 in Table 1) of the following formula

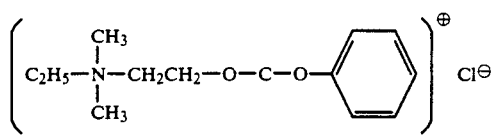

in a yield of 78.5%.

PRODUCTION EXAMPLE 5

A mixture of 2.65 g (0.02 mole) of N,N-dimethylcarbamoylethanolamine, 1.6 g (0.025 mole) of chloroethane and 10 ml of acetonitrile was heated at 100° C. for 5 hours in a 100 ml autoclave, and the solvent was evaporated by an evaporator. The resulting crystals were recrystallized from ethanol-ether to give a compound of the formula

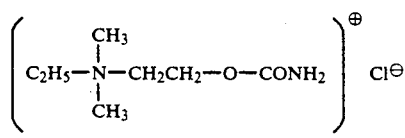

(compound No. 26 in Table 1) in a yield of 27.9%.

PRODUCTION EXAMPLE 6

3.07 g (0.02 mole) of a compound of the formula

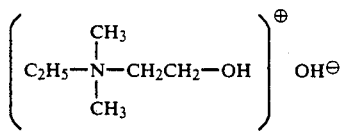

in the form of a solid was gradually added to 11.29 g (0.1 mole) of chloroacetyl chloride, and the mixture was stirred at room temperature for 5 hours. Ether was added, and the resulting oily precipitate was separated, washed with ether, and crystallized. The crystals were recrystallized from ethanol-ether to give a compound of the formula

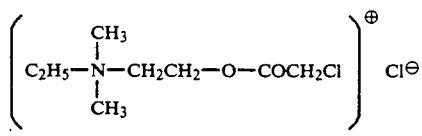

(compound No. 24 in Table 1) in a yield of 70.8%.

In the same way as in Production Examples 1 to 6, the compounds of formula (I) or salts thereof shown in Table 1 can be obtained. Table 1 also describes the compounds obtained in Production Examples 1 to 6.

TABLE 1

| Compound No. | R | X | Salt | IR peak (cm$^{-1}$) | | | |
|---|---|---|---|---|---|---|---|
| | | | | OH stretching | CH deformation | C—O stretching | Others |
| 1 | $C_2H_5$ | H | Br | 3650–3050 | 1460 | 1080 | |
| 2 | $CH_3$\\$CH_3$/CH | H | Br | 3650–3050 | 1475 | 1080 | |
| 3 | $CH_3CH_2CH_2CH_2$ | H | Br | 3650–3050 | 1485 | 1045 | |

TABLE 1-continued

| | R | | X | Salt | | | | Others |
|---|---|---|---|---|---|---|---|---|
| 4 | $CH_2=CHCH_2$ | | H | Cl | 3650–3000 | $\{\begin{array}{c}1460\\950\end{array}$ | 1080 | C=C stretching 1640 |
| 5 | $CH_3CH_2CH_2$ | | H | Br | 3650–3050 | 1460 | 1070 | |
| 6 | $CH_2=C(CH_3)CH$ | | H | Br | 3650–3050 | $\{\begin{array}{c}1470\\930\end{array}$ | 1080 | C=C stretching 1635 |
| 7 | $(CH_3)_2CHCH_2$ | | H | Br | 3650–3070 | 1475 | 1055 | |
| 8 | $(CH_3)_2C=CHCH_2$ | | H | Br | 3650–3080 | 1470 | 1045 | |
| 9 | $CH_2=CHCH_2CH_2$ | | H | Br | 3650–3100 | 1480 | 1085 | C=C stretching 1640 |
| 10 | $(CH_3)_3C$ | | H | Br | 3650–3100 | 1470 | 1080 | |
| 11 | $CH\equiv CCH_2$ | | H | Br | 3550–3050 | 1455 | 1085 | C≡C stretching 2130 |
| 12 | $CH_3CH=CHCH_2$ | | H | Br | 3650–3080 | 1460 | 1090 | |
| 13 | $CH_3CH_2-C(CH_3)_2$ | | H | Br | 3650–3010 | 1470 | 1080 | |

| Compound No. | R | X | Salt | IR peak (cm⁻¹) C=O stretching | C—O stretching | Others |
|---|---|---|---|---|---|---|
| 14 | $C_2H_5$ | $COCH_3$ | Br | 1745 | 1230 | |
| 15 | $n\text{-}C_3H_7$ | $COCH_3$ | Br | 1750 | 1240 | |
| 16 | $CH_2=CHCH_2$ | $COCH_3$ | Cl | 1740 | 1230 | |
| 17 | $CH_2=C(CH_3)CH_2$ | $COCH_3$ | Cl | 1745 | 1240 | C=C stretching 1650 |
| 18 | $C_2H_5$ | $COC_6H_5$ | Cl | 1730 | 1270 | C—H out-of-plane deformation 715 |
| 19 | $n\text{-}C_3H_7$ | $COC_6H_5$ | Cl | 1720 | 1270 | C—H out-of-plane deformation 710 |
| 20 | $CH_2=C(CH_3)CH_2$ | $COC_6H_5$ | Cl | 1730 | 1275 | C—H out-of-plane deformation 710<br>C=C stretching 1640 |
| 21 | $C_2H_5$ | $COC_2H_5$ | Br | 1735 | 1180 | |
| 22 | $C_2H_5$ | $COCH(CH_3)_2$ | Br | 1730 | 1200 | |
| 23 | $C_2H_5$ | $PO_3H_2$ | Br | — | — | P—O stretching 1080<br>P=O stretching 1190 |
| 24 | $C_2H_5$ | $COCH_2Cl$ | Cl | 1720 | 1160 | |
| 25 | $CH_2=CHCH_2$ | $COCH_2Cl$ | Cl | 1740 | 1170 | |
| 26 | $C_2H_5$ | $CONH_2$ | Cl | 1725 | 1320 | NH deformation 1620 |
| 27 | $C_2H_5$ | $COOCH_3$ | Cl | 1760 | 1280 | |
| 28 | $CH_2=CHCH_2$ | $COC_6H_5$ | Cl | 1730 | 1270 | C—H out-of-plane deformation 710 |
| 29 | $C_2H_5$ | $CO(CH_2)_4CH_3$ | Cl | 1720 | 1200 | |
| 30 | $C_2H_5$ | H | $PO_3H_2$ | — | — | |

Among these compounds, compounds Nos. 1, 3, 6, 14, 17 and 22 are preferred. Compounds Nos. 6, 14 and 17 are particularly preferred because they are effective at low dosages.

The compounds of formula (I) or their agriculturally acceptable salts (to be generically referred to as the active compound of the invention) have the ability to increase the photosynthetic action and/or root-forming action of plants and to promote the growth of the plants. There is no particular limitation on the plants whose growth can be promoted in accordance with this invention, and they may include various agriculturally or horticulturally cultivated plants. Specific examples include cereal plants such as rice, wheat, barley, and corn, leguminous plants such as soybean; plants having underground tubers or bulbs such as onion, garlic and potato; vegetables grown for their edible roots such as beet and carrot; fruits such as peach, persimmon, grape and apple; vegetables grown for their edible fruits such as tomato and cucumber; vegetable grown for their edible leaves such as lettuce, cabbage, cauliflower and spinach; and flowers such as tulip and cosmos.

The active compound of this invention may be formulated for application in any known form, such as a wettable powder, granules, an aqueous solution, an emulsifiable concentrate or an aqueous suspension, using a conventional agriculturally acceptable carrier or diluent. There is no special restriction on the carrier or diluent used in the formulation so long as they are agriculturally acceptable. For example, talc and bentonite may be used as a carrier for a wettable powders and granules. The aqueous solution is most preferred as the form in which the active compound is applied.

The resulting formulations may contain the active compound of the invention in an amount of 1 to 75% by weight, preferably 30 to 75% by weight. Such formulations may further contain another conventional agriculturally active ingredient such as a fertilizer, insecticide or bactericide.

The formulations may desirably contain a surfactant. The amount of the surfactant is, for example, 0.02 to 20% by weight, preferably 0.1 to 5% by weight, depending upon the form of the formulation to promote the adsorption and penetration of the active ingredients. Preferred surfactants may include nonionic surfactants such as polyoxyethylene alkyl ethers (e.g. polyoxyethylene lauryl ether), and anionic surfactants such as lauryl sulfonate triethanolamine salt.

The active compound of this invention may be applied by any methods known per se. For example, it may be sprayed onto the stalks and leaves of mature plants, or poured onto parts near the roots. Seeds are preferably immersed in a solution containing the active compound of the present invention.

The rate of application of the active compound of the invention varies, for example, with the type of a plant to be treated, the stage of plant growth, and the manner and timing of application. For example, for spraying onto the stalks and leaves of a plant, the rate of application of the active compound of the invention normally ranges from 25 to 3,000 g, preferably from 50 to 2,000 g, per hectare of the cultivated area. An aqueous solution is a preferred type of formulation for foliar application, and may contain the active compound of the invention in a concentration of 100 to 100,000 ppm, particularly 200 to 50,000 ppm.

Generally, the good time of applying the active compound of the invention is when photorespiration of the plant is at its peak. For example, it is desirably applied at some point during a period from the reproductive growth to the harvesting time. To some plants, however, application during vegetative growth may provide more desirable effects. In other words, there is no specific limit to the timing of application.

In the case of pouring the active compound of the invention, it is usually advantageous to apply an aqueous solution containing the active compound of the invention in a concentration of 1 to 5,000 ppm, preferably 5 to 1,000 ppm, to parts near the roots of a plant at a rate of 10 to 100 m$^3$, preferably 20 to 50 m$^3$, per hectare.

When the active compound of this invention is used to treat plant seeds, it is suitable to immerse the seeds in an aqueous solution normally containing 0.05 to 2,000 ppm, preferably 0.1 to 1,000 ppm, for about 1 to about 48 hours, preferably about 4 to about 24 hours.

To use the active compound of the invention for root formation or anchoring of rice seedlings, it is the general practice to pour an aqueous solution of the active compound onto the roots of the rice seedlings before transplantation, preferably at least 10 days before transplantation.

The method, time and rate of application and the expected effect of the active compound of the invention on typical plants are summarized in Table 2.

| Crop | Method of application | Time of application | Rate of application | Expected effect |
|---|---|---|---|---|
| rice, wheat, barley | foliar | from 40 days before heading to 10 days after heading | 100–2000 g/ha | increased harvest |
| soybean (leguminous plants) | foliar | from 10 days before flowering to 20 days after flowering | 50–1000 g/ha | increased harvest (increased number of pods) |
| onion, garlic tulip | foliar | early stage of bulb swelling | 50–1000 g/ha | bulb swelling |
| potato | foliar | early stage of tuber growth | 50–1000 g/ha | tuber growth and increased yield |
| peach, persimmon, grape, apple | foliar | flowering stage to 10 days before harvest | 10–2000 g/ha | size increase of fruits, increase of sweetness, maintenance of freshness |
| wheat, barley | foliar | 2- to 3-leaf stage | 50–1000 g/ha | growth promotion |
| rice | seed treatment | immersed for 24 hours after immersion in water for 2 days | 0.1–1000 ppm | promotion of growth and root formation |
| wheat, barley | seed treatment | immersed for 24 hours | 0.1–1000 ppm | promotion of growth and root formation |
| tomato, lettuce | seed treatment | immersed for 24 hours | 1–300 ppm | promotion of growth and root formation |
| rice seedling | pouring | from the 2-leaf stage to the time before transplantation | 5–500 mg /1800 cm$^2$ (10–1000 ppm) | promotion of growth and root formation |
| tomato seedling | pouring | seedling stage | 1–100 mg seedling (10–1000 ppm) | growth promotion |

By applying the compound of formula (I) or its agriculturally acceptable salt to a plant in accordance with this invention, the photosynthetic action and rootforming action of the plant can be greatly increased, and consequently, the growth of the plant can be promoted. For example, the active compound of this invention can promote the root formation of $C_3$ plants such as rice, wheat, barley, beet, sweet potato, potato and onion and $C_4$ plants such as corn and sugarcane, nurse their sound seedlings, promote their growth in the early stage, and incrase the harvest of the crops. Furthermore, it can increase the sweetness and size of fruits such as apple, persimmon, peach, orange and lemon, promote their coloration, and maintain their freshness. It can further promote size increase of bulbs of flowers such as tulip, and promote the flowering of cosmos, etc.

For application of the active compound of the invention to plants, it may be formulated into a wettable powder, an aqueous solution, a suspension in water or oil, etc. Typical formulation examples are given below.

FORMULATION EXAMPLE 1

Aqueous solution:

Fifty grams of compound No. 4, 10 g of polyoxyethylene oleyl ether and 10 g of triethanolamine lauryl sulfate and 180 g of pure water are mixed to prepare an aqueous solution containing 20% of compound No. 4. Usually, it is used after it is diluted to 100 to 1000 times.

FORMULATION EXAMPLE 2

Wettable powder:

Fifty grams of compound No. 20, 2 g of sodium dodecylbenzenesulfonate, 1 g of polyoxyethylene alkyl aryl ether, 10 g of talc, and 37 g of bentonite are uniformly mixed and pulverized to give a wettable powder containing 50% of compound No. 20.

The excellent plant growth promoting activity of the active compounds of this invention are demonstrated by the following Test Examples.

TEST EXAMPLE 1

Photosynthesis using protoplasts:

Wheat (Variety: Norin No. 61) was cultivated for 10 days in vermiculite as soil in a phytotron kept at 25° C. in the day time under natural light and 20° C. at night. Protoplasts were isolated from the wheat by a conventional method [see Plant Physiol. (1978), 62, 313–319]. The effect of the protoplasts on photosynthesis was examined in the following manner using an oxygen electrode.

The protoplasts were incubated for 1 minute with the test compound in a reaction solution [HEPES-KOH buffer (pH 7.6), 0.4M sorbitol, 1 mM EDTA, 0.3mM sodium hydrogen carbonate], and then light (100,000 lux) was irradiated to initiate photosynthesis. The activity was examined in comparison with a non-treated lot (containing no test compound). The results are shown in Table 3.

TABLE 3

| Compound No. | Concentration (mM) | Increase in photosynthesis* |
|---|---|---|
| 1 | 10 | +++ |
| 2 | " | ++ |
| 3 | " | ++++ |
| 4 | " | ++++ |
| 5 | " | +++ |
| 6 | " | ++++ |
| 7 | " | ++ |
| 8 | " | ++ |
| 9 | " | +++ |
| 10 | " | ++ |
| 11 | " | +++ |
| 12 | " | +++ |
| 14 | " | +++ |
| 15 | " | ++ |
| 16 | " | ++ |
| 17 | " | +++ |
| 18 | " | +++ |
| 19 | " | +++ |
| 22 | 0.01 | +++ |
| 23 | " | ++ |
| 28 | " | +++ |
| 30 | 0.1 | +++ |
| Choline chloride (comparison) | 10 | + |

*—: Decreased from that in the non-treated lot.
±: Same as that in the non-treated lot.
+: 0–5% increase from that in the non-treated lot.
++: 5–10% increase from that in the non-treated lot.
+++: 10–15% increase from that in the non-treated lot.
++++: More than 15% increase from that in the non-treated lot.

TEST EXAMPLE 2

Seeds of wheat were caused to absorb water, and divided into two groups. Each group of seeds were sown on a predetermined amount of vermiculite and cultivated for 10 days in a natural light phytotron kept at 25° C. in the day time and 20° C. at night. An aqueous solution containing the test compound and 200 ppm of polyoxyethylene alkyl aryl ether (surfactant) was sprayed onto the plant. Four, and 6 days later, protoplasts were isolated from the wheat, and the photosynthetic activity per chlorophile was measured by an oxygen electrode method with regard to both a lot treated with the test compound and a non-treated lot. The results are shown in Table 4.

TABLE 4

| Compound No. | Spray concentration (ppm) | Activity ratio to the non-treated lot | |
|---|---|---|---|
| | | 4 days | 6 days |
| 1 | 300 | 115 | 112 |
| 4 | 300 | 109 | 115 |

TEST EXAMPLE 3

Five rice seeds (variety: Nihonbare) germinated to about 2 mm were put into each of test tubes, and 1 ml of an aqueous solution of the test compound (adjusted to pH 7) was added. (Only water was added to a non-treated lot). The seeds were grown at 25° C. under artificial light, and on the 9th day, the length of the overground portion (stalks and leaves) of each plant and the length of the longest root were measured. The results are shown in Table 5.

TABLE 5

| Compound No. | Concentration (mM) | Overground portion (ratio to the non-treated lot) | Root portion (ratio to the non-treated lot) |
|---|---|---|---|
| Non-treated | — | 100 (8.4 mm) | 100 (4.0 mm) |
| 1 | 1 | 96 | 143 |
|  | 0.3 | 104 | 124 |
| 3 | 1 | 101 | 135 |
|  | 0.3 | 105 | 127 |
| 4 | 1 | 120 | 118 |
|  | 0.3 | 110 | 125 |

TEST EXAMPLE 4

About 1 liter pots were filled with soil, and seeds of corn and soybean were sown. An aqueous solution of the test compound was sprayed onto the surface of the leaves at a rate of 1 ml per pot 14 days after sowing in the case of corn and 30 days after sowing in the case of soybean. Twenty days after the spraying, the overground portions (stalks and leaves) of both of these crops were reaped, and weighed. The results are shown in Table 6.

TABLE 6

| Compound No. | Concentration (ppm) | Ratio to the non-treated lot | |
|---|---|---|---|
| | | Corn | Soybean |
| 4 | 1000 | 128 | 117 |
|  | 500 | 129 | 115 |
| 3 | 1000 | 115 | 114 |
|  | 300 | 113 | 117 |
| 6 | 1000 | 132 | 119 |
|  | 300 | 125 | 115 |
| Non-treated lot | — | 100 (2.41 g per plant) | 100 (7.53 g per plant) |

TEST EXAMPLE 5

Each of the test compounds in each of the dosages shown in Table 7 was dissolved in 1000 liters of water, and 200 ppm of polyoxyethylene alkyl aryl ether was added as a surfactant. On May 10, the solution was sprayed onto the leaves of wheat (variety: winter wheat "horoshiri") 30 days before flowering. On July 26, the wheat was harvested, and the dry weight of the overground portions (stalks and leaves) and the amount of harvest were measured.

In the non-treated lot, only a mixture of water and the surfactant was sprayed.

The test results are shown in Table 7.

TABLE 7

| Compound No. | Dosage (g/ha) | Dry weight of the overground portions | | Amount of harvest | |
|---|---|---|---|---|---|
| | | kg/ha | Ratio to the non-treated lot | kg/ha | Ratio to the non-treated lot |
| Non-treated | — | 14040 | 100 | 5870 | 100 |
| 6 | 600 | 15920 | 113 | 6990 | 119 |
| | 300 | 16830 | 120 | 7510 | 128 |
| 14 | 600 | 18790 | 118 | 7280 | 124 |
| | 300 | 16430 | 117 | 7220 | 123 |
| 17 | 600 | 16150 | 115 | 7040 | 120 |
| | 300 | 16710 | 119 | 7280 | 124 |

TEST EXAMPLE 6

Paddy soil was filled in Wagner pots (1/5000 a), and a chemical fertilizer (nitrogen content 10%, phosphorus content 24%, potassium content 16%) was applied to the soil as a base fertilizer at a rate of 2 g/pot. On May 25, 6 rice seedlings (variety: "koshihikari") were transplanted in each pot, and cultivated in a greenhouse. On August 7 (immediately after heading), an aqueous solution of each of the test compounds shown in Table 8 in the concentrations indicated (containing 200 ppm of polyoxyethylenealkyl aryl ether as a surfactant) was sprayed onto the leaves of the rice plants.

On September 20, the rice plants were reaped, and the amount of refined rice was examined. The results are shown in Table 8. In the non-treated lot, only a mixture of the surfactant and water was sprayed.

TABLE 8

| Compound No. | Dosage (g/ha) | Amount of refined rice harvested as ratio to the non-treated lot (%) |
|---|---|---|
| Non-treated | — | 100 (19.8 g/pot) |
| 3 | 1000 | 117 |
| | 300 | 135 |
| 4 | 1000 | 127 |
| | 300 | 122 |
| 6 | 1000 | 117 |
| | 300 | 144 |
| 14 | 1000 | 132 |
| | 300 | 141 |
| 15 | 1000 | 116 |
| | 300 | 115 |
| 16 | 1000 | 126 |
| | 300 | 115 |
| 17 | 1000 | 128 |
| | 300 | 143 |
| 22 | 1000 | 124 |
| | 300 | 128 |
| 28 | 1000 | 114 |
| | 300 | 115 |

TEST EXAMPLE 7

On December 21, wheat (variety: Norin No. 61) was sown in pots (1/85500 a). On January 6 (after half a month from sowing), three individuals of wheat (2.5-leaf) having the same growth state were left per pot, and the rest were cut off at the roots. An aqueous solution of each of the test compounds indicated in Table 9 and choline chloride as a comparison in a concentration of 1000 ppm was sprayed onto the wheat plants at a rate of 1 ml per pot. On March 5 (after 2 months), the weight of the overground portions (stalks and leaves) in the fresh state and dried state (after drying at 105° C. for 24 hours), and the height of the overground portions were measured. This test was carried out in a glass greenhouse using a set of 4 test lots.

The results are shown in Table 9.

TABLE 9

| Compound No. | Ratio to the non-treated lot (%) | | |
|---|---|---|---|
| | Height | Fresh weight | Dry weight |
| Non-treated | 100 (29.3 cm) | 100 (2.53 g per plant) | 100 (0.64 g per plant) |
| 4 | 114 | 135 | 144 |
| 5 | 115 | 139 | 141 |
| 6 | 119 | 140 | 148 |
| 16 | 120 | 143 | 142 |
| Choline chloride | 100 | 105 | 105 |

TEST EXAMPLE 8

An aqueous solution containing 100 ppm of each of compounds Nos. 1 and 6 and 200 ppm of polyoxyethylene alkyl aryl ether as a surfactant was sprayed on all over persimmon trees (seedless variety) at a rate of 2500 liters/ha by a power sprayer one month before harvest. After harvesting, the persimmon fruits were sealed up in polyethylene bags together with 0.8% by weight, based on the weight of the fruits, of 38% ethanol, and allowed to stand at room temperature for 10 days to remove tannin. After opening the bags, the weight, sweetness degree and freshness maintenance of the fruits were measured. The results are shown in Table 10.

TABLE 10

| Compound No. | On the day of harvest | | After tannin removal | |
|---|---|---|---|---|
| | Average fruit weight (g) | Color of the top of the fruit | Average sweetness degree (Brix, %) | Average day lapsed until softening |
| Non-treated | 129.6 | 5.65 | 17.0 | 4.0 |
| 1 | 132.4 | 6.01 | 18.0 | 20.0 |
| 6 | 141.1 | 6.21 | 18.4 | 25.0 |

TEST EXAMPLE 9

Cotton was spread at the bottom of a tubular bottle having a diameter of 5 cm, and 10 ml of an aqueous solution of each of the test compounds indicated in Table 11 and choline chloride as a comparison in a concentration of 1 ppm was added. Six seeds of lettuce whose germination had been forced were put on the bottom of the bottle in a circle, and grown at 25° C. under natural light (1500 lux) for 7 days. Then, the lengths of the overground portion (stalks and leaves) and the root portion were measured. The results are shown in Table 11.

TABLE 11

| Compound No. | Length as a ratio to the non-treated lot (%) | |
|---|---|---|
| | foliar portion | root portion |
| Non-treated | 100 (15.8 mm) | 100 (19.9 mm) |

TABLE 11-continued

| Compound No. | Length as a ratio to the non-treated lot (%) | |
|---|---|---|
| | foliar portion | root portion |
| 1 | 148 | 137 |
| 3 | 101 | 130 |
| 5 | 128 | 126 |
| Choline chloride | 105 | 107 |

What is claimed is:

1. A plant growth promoting composition comprising
(1) at least one active compound selected from the group consisting of compounds of the formula

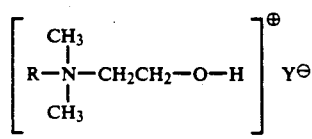 (I)

wherein R represents a $C_{3-4}$ alkyl or $C_{3-4}$ alkenyl group, and Y represents a chlorine or a bromine atom, and
(2) an agriculturally acceptable carrier or diluent.

2. A method of promoting the growth of plants, which comprises applying an effective amount of at least one active compound selected from the group consisting of compounds of the formula

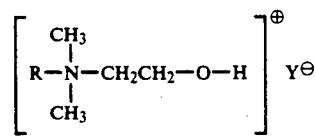 (I)

wherein R represents a $C_{3-4}$ alkyl or $C_{3-4}$ alkenyl group, and Y represents a chlorine or a bromine atom, to the stalks, leaves roots or seeds of the plants.

3. The method of claim 2 wherein the active compound is applied in the form of an aqueous solution.

4. The method of claim 2 wherein the aqueous solution contains 0.02 to 20% by weight of a surfactant.

5. The method of claim 2 wherein the active compound is applied in the form of an aqueous solution to the stalks and leaves of mature plants at a rate of 25 to 3,000 g per hectare of the cultivated area for the plants.

6. The method of claim 2 wherein seeds of the plants are immersed in an aqueous solution containing the active compound in a concentration of 0.05 to 2,000 ppm.

7. The method of claim 2 wherein an aqueous solution containing the active compound in a concentration of 1 to 5,000 ppm is poured onto parts near the roots of seedlings of the plants.

8. The method of claim 2 wherein the plant is wheat.

9. The method of claim 2 wherein R represents $C_{3-4}$ alkenyl.

* * * * *